United States Patent
Hale et al.

(10) Patent No.: US 6,695,774 B2
(45) Date of Patent: Feb. 24, 2004

(54) APPARATUS AND METHOD FOR CONTROLLING ENDOSCOPIC INSTRUMENTS

(75) Inventors: Eric L. Hale, South Pasadena, CA (US); Nathan J. Schara, Pasadena, CA (US); Hans D. Høeg, Arcadia, CA (US)

(73) Assignee: EndActive, Inc., Arcadia, CA (US)

( * ) Notice: Subject to any disclaimer, the term of this patent is extended or adjusted under 35 U.S.C. 154(b) by 0 days.

(21) Appl. No.: 10/036,594

(22) Filed: Dec. 31, 2001

(65) Prior Publication Data

US 2002/0099263 A1 Jul. 25, 2002

Related U.S. Application Data

(60) Provisional application No. 60/262,297, filed on Jan. 19, 2001.

(51) Int. Cl.$^7$ ................................ A61B 1/045
(52) U.S. Cl. ................ 600/173; 600/103; 600/117; 600/118; 600/137; 356/241.3
(58) Field of Search ................ 600/103, 109, 600/117, 118, 137, 146, 173, 160; 356/241.3; 606/1; 348/65

(56) References Cited

U.S. PATENT DOCUMENTS

| 4,697,577 A |   | 10/1987 | Forkner |
|---|---|---|---|
| 5,313,306 A | * | 5/1994 | Kuban et al. .................. 348/65 |
| 5,496,260 A | * | 3/1996 | Krauter et al. ............... 600/148 |
| 5,908,436 A | * | 6/1999 | Cuschieri et al. ............ 606/205 |
| 5,954,634 A | * | 9/1999 | Igarashi ....................... 600/109 |

FOREIGN PATENT DOCUMENTS

| WO | WO 99/42028 | 8/1999 |
|---|---|---|
| WO | WO 01/22865 | 4/2001 |

* cited by examiner

*Primary Examiner*—John Mulcahy
(74) *Attorney, Agent, or Firm*—Morrison & Foerster

(57) ABSTRACT

A control and indicator apparatus for a variable direction-of-operation endoscopic instrument comprises a handle, a coinciding pointer, and a linking system connecting the handle to the endoscopic instrument. The handle affords the user intuitive and integrated control of the available degrees of freedom and the pointer conveys to the user the direction and orientation of the endoscopic working vector by shadowing its movement.

13 Claims, 6 Drawing Sheets

APPARATUS AND METHOD FOR CONTROLLING ENDOSCOPIC INSTRUMENTS

CROSS-REFERENCE TO RELATED APPLICATIONS

This application claims the benefit of U.S. provisional application Ser. No. 60/262,297, filed Jan. 19, 2001, entitled "Apparatus and Method for Controlling and Indicating the Direction and Orientation of the Distal Portion of Endoscopic Instruments," the contents of which are incorporated herein by reference.

FIELD OF THE INVENTION

The present invention relates to variable direction-of-view endoscopes (including devices such as borescopes, fiberscopes, etc.) and to variable direction-of-operation endoscopic tools used for viewing the inside of cavities and for performing other tasks within enclosed spaces.

BACKGROUND OF THE INVENTION

Endoscopic instruments typically have a long primary axis along which they are inserted into the work or examination site. They also have a working vector that may or may not coincide with this primary axis. In the case of a viewing device, the working vector is generally defined as the view vector radiating from the distal end of the optical system and continuing through the center of the field of view. In the case of other endoscopic instruments, the working vector could be defined as the centerline of a gripper, the path of an emitted laser, etc., as appropriate to the given tool. Many of these instruments also have a rotational orientation about the working vector, examples of which are the rotation of the image viewed with an endoscope or the orientation of the plane of a two-jawed gripper.

Variable direction endoscopic instruments have an adjustable working vector. An example of such an instrument is a variable direction-of-view endoscope as disclosed in U.S. Pat. No. 4,697,577 to Forkner (1987), in WIPO publication WO 99/42028 by Høeg et al. (1999), and in WIPO publication WO 01/22865 by Ramsbottom (2001). One of the biggest challenges for the user of such an endoscope or other variable direction endoscopic instrument is visualizing the working vector inside the structure being investigated. Because the tip of an endoscopic instrument is concealed during operation, the user cannot see its position and configuration relative to the surroundings, and such instruments generally do not have a good way of conveying tip configuration, direction, and orientation to the user and observers. In some cases round dials or indicator marks are used to show the position of a tool with respect to a certain axis, but these features fail to provide the user with a real sense of the working vector. A partial attempt to solve this problem was disclosed in WIPO publication WO 99/42028 by Høeg et al. (1999) wherein a variable direction-of-view endoscope is provided with a proximal control knob marker which indicates the direction of the distal view vector. This solution is limited, however, in that it provides the user information about only the direction-of-view and not its orientation, and also fails to give the user a true feel for the actual working vector.

The endoscopes discussed above appear to have one degree of freedom. However, as specified in Haag at al, a primary mode of operation involves rotating the endoscope about its longitudinal axis to provide some control of the viewing direction. Because this rotation provides an additional degree of freedom for the view vector it is considered a second degree of freedom of the endoscope. An endoscopic system in which the view orientation may be changed has yet another degree of freedom.

Another type of endoscope capable of varying its viewing direction is disclosed in U.S. Pat. No. 5,496,260 to Krauter at al. (1996). This design has a deflectable tip which is actuated by a pair of knobs at the proximal end of the instrument. The indicator marks on the knobs only provide a general estimate of the amount of bending in each plane. Users have difficulty determining the exact viewing angle and orientation of this type of endoscope.

Yet another class of endoscopes that is considered capable of varying their direction of view includes those disclosed in U.S. Pat. No. 5,954,634 to Igarashi (1998) and U.S. Pat. No. 5,313,306 to Kuban, et al. (1994). These devices provide a viewed area variably selected from within a wide-angle field. The user controls the viewing direction within the wide-angle field Through a joystick, keypad, or other similar input device. There is no facility disclosed communicating viewing direction or orientation to the user.

At best, prior art indication methods only accomplish the feedback function of indirectly conveying the endoscopic working direction and orientation back to the user. They do not provide a way for the user to intuitively control these parameters. Current control methods use knob or trigger mechanisms to manipulate the working vector and are limited in that they only allow the control of one degree of freedom per knob, prohibiting intuitive and integrated control of multiple degrees of freedom. Also, control mechanisms for endoscopic instruments have generally been designed to drive the instrument mechanics without regard for showing the user how the control input affects the configuration of the instrument.

From the discussion above, it should become apparent that there is a need for an integrated control mechanism and an integrated indicator mechanism that will provide intuitive and simultaneous control of multiple degrees of freedom of an endoscopic instrument, provide an effective representation of the direction and orientation of the working vector of an endoscopic instrument, provide an understanding of the spatial configuration of the instrument, provide a clear relationship between two or more distinct working configurations (a feature particularly useful in procedures where the user must shift between distinct directions), provide a clear physical representation of the working vector of the endoscopic instrument to observers (such as technicians, nurses, and assistant surgeons), provide a more comfortable user interface which does not necessarily have to coincide with the actual mechanics of the endoscopic instrument, and provide a consistent control scheme for multiple instruments.

BRIEF SUMMARY OF THE INVENTION

In accordance with the present invention, a control and indicator apparatus for a variable direction-of-operation endoscopic instrument comprises a handle, a pointer, and a linking system connecting the handle to the endoscopic instrument. The handle affords the user intuitive and integrated control of the available degrees of freedom and the pointer conveys to the user the direction and orientation of the endoscopic working vector by shadowing its movement The control and indicator apparatus can be positioned off of the body of the endoscopic instrument or built directly thereon. The apparatus can be linked to the working vector through a mechanical or electromechanical system.

The term "endoscopic instrument" as used herein is defined as an endoscope (used for medical procedures), any similar device such as a borescope, a fiberacope, etc. or any tool for performing tasks within the enclosed spaces viewed using these devices. The term "working vector" as used herein is defined on a viewing device as the view vector radiating from the distal end of the optical system and continuing through the center of the field of view or on a tool as the centerline of the gripper, the path of the emitted laser, etc., as appropriate to the given tool. The term "working orientation" as used herein is defined on a. viewing device as the orientation of the output image, e.g. "up" as viewed on an output monitor, or on a tool as the rotational orientation about the working vector.

What is claimed is an apparatus for aiding in the interpretation of a working vector of a variable direction-of-operation endoscopic instrument comprising at least two degrees of freedom, said apparatus comprising a pointing means for indicating a direction, and a linking means for connecting said pointing means to said endoscopic instrument, wherein said direction of said pointing means is related to a working direction of said endoscopic instrument.

DETAILED DESCRIPTION OF THE INVENTION

Figure 1:
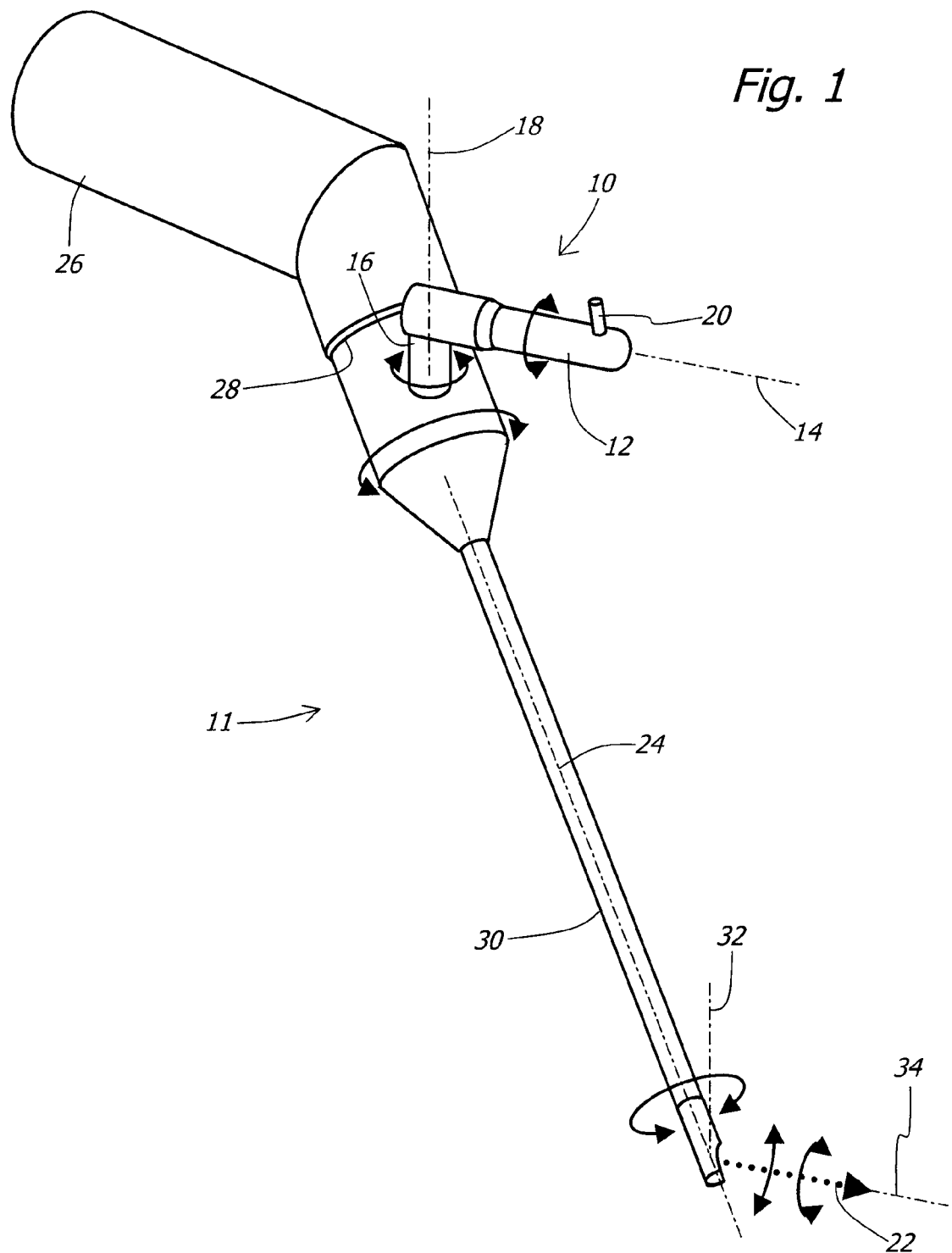
FIG. 1 shows a variable direction-of-view endoscope with an integrated three degree of freedom direction and rotation control handle and coinciding pointer assembly according to the preferred embodiment of the present invention.

The following detailed description illustrates the invention by way of example, not by way of limitation of the principles of the invention. This description will clearly enable one skilled in the art to make and use the invention and describes several embodiments, adaptations, variations, alternatives and uses of the invention, including what we presently believe is the best mode of carrying out the invention. The invention will be described by way of illustration in conjunction with the attached drawings in which like reference numerals refer to like elements.

FIG. 1 shows an integrated three degree of freedom direction and orientation control handle and coinciding pointer assembly 10 on a variable direction-of-view endoscope 11, according to a preferred embodiment of the present invention. The handle-pointer assembly 10 comprises a handle 12 which can rotate about a first axis 14 and a base 16 which can rotate about a second axis 18. The handle 12 has an orientation indicator 20 that indicates the current orientation of the endoscopic working vector 22, which always remains parallel to the handle 12 and its axis 14. When the endoscope hand piece 26 is held, a rotary joint 28 allows the entire handle-pointer assembly 10 to be rotated about a third axis 24 to cause the endoscope shaft 30 to spin. By manipulating the handle-pointer assembly 10, the working vector 22 can be made to rotate about the third axis 24, a forth axis 32 and a fifth axis 34 to parallel the changing direction of the first axis 14 and the changing orientation of the indicator 20. It should be noted that axes 34 and 32 are parallel to the first axis 14 and the second axis 18, respectively. With the degrees of freedom available, any working direction and orientation can be selected intuitively by pointing the handle 12 towards a target and spinning it as desired while the direction and orientation of the handle 12 show the configuration of the working vector 22.

Figure 2:
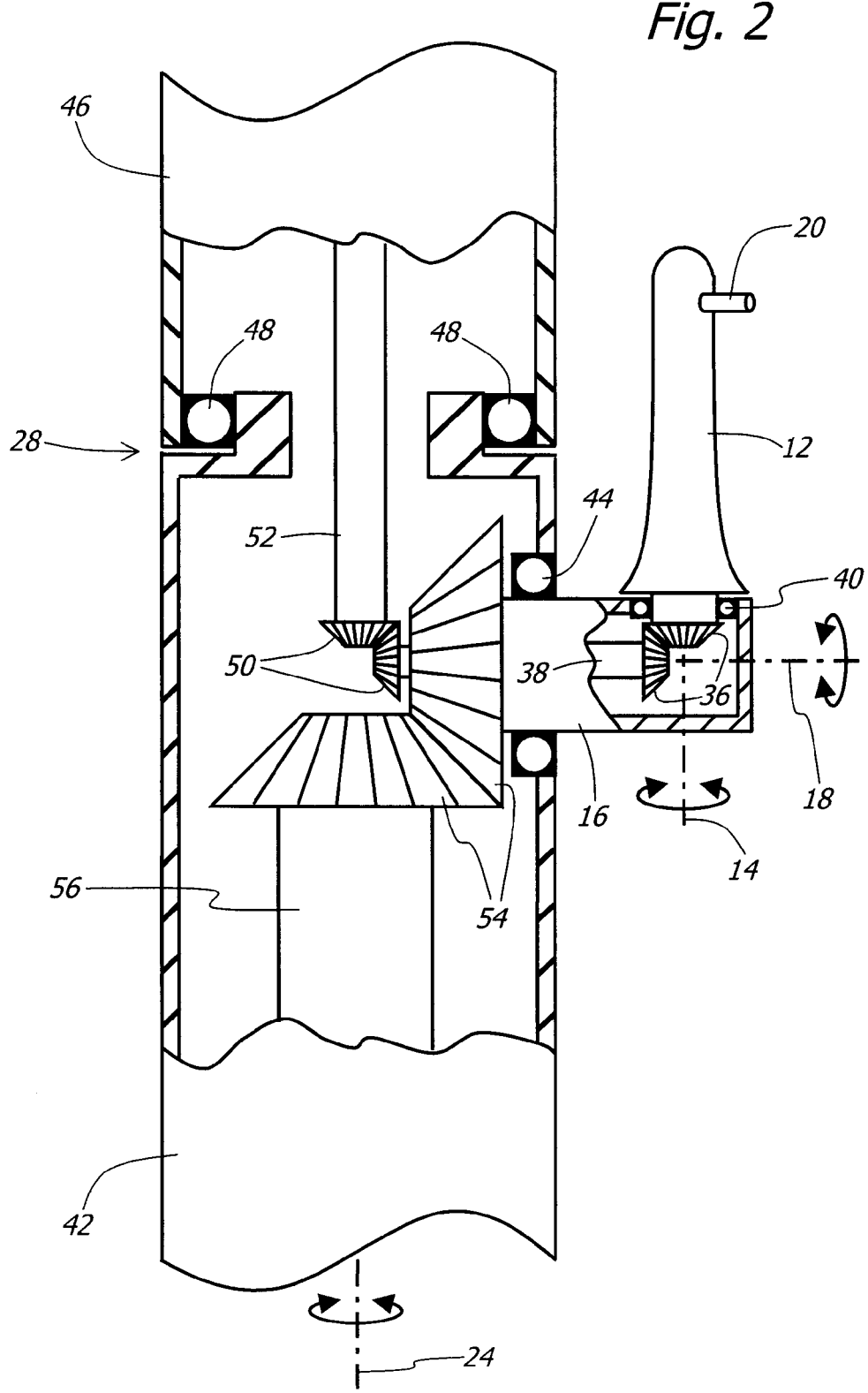
FIG. 2 is a cutaway view of an integrated mechanical three degree of freedom direction and rotation control handle and coinciding pointer assembly implemented with a gear differential according to an embodiment of the present invention.

FIG. 2 illustrates an embodiment of an integrated mechanical three degree of freedom handle and coinciding pointer assembly. A base 16 houses a pair of gears 36 which transmits rotary motion of the handle 12 about a first axis 14 to an internal shaft 38, which rotates independently of the base 16 about a second axis 18. The handle 12, having an orientation indicator 20, is anchored to the base 16 by a bearing 40. The base 16 is anchored to a forward portion of the instrument frame 42 by a bearing 44. The forward portion of the instrument frame 42 is anchored to a backward portion of the instrument frame 46 by a bearing 48, which forms a rotary joint 28. A second set of gears 50 transmits rotary motion of the internal shaft 38 to a shaft 52, which in the described embodiment controls the orientation of the working vector (not shown) and which can rotate independently of either the forward or backward portion of the instrument frame 42, 46. A third set of gears 54 transmits rotary motion of the base 16 to a shaft 56, which controls the direction of the working vector (not shown) about one axis (not shown). The handle 12 can also be used to rotate the forward portion of the instrument frame 42, and thereby the working vector (not shown), relative to the backward portion of the instrument frame 46 about a third axis 24.

Figure 3:
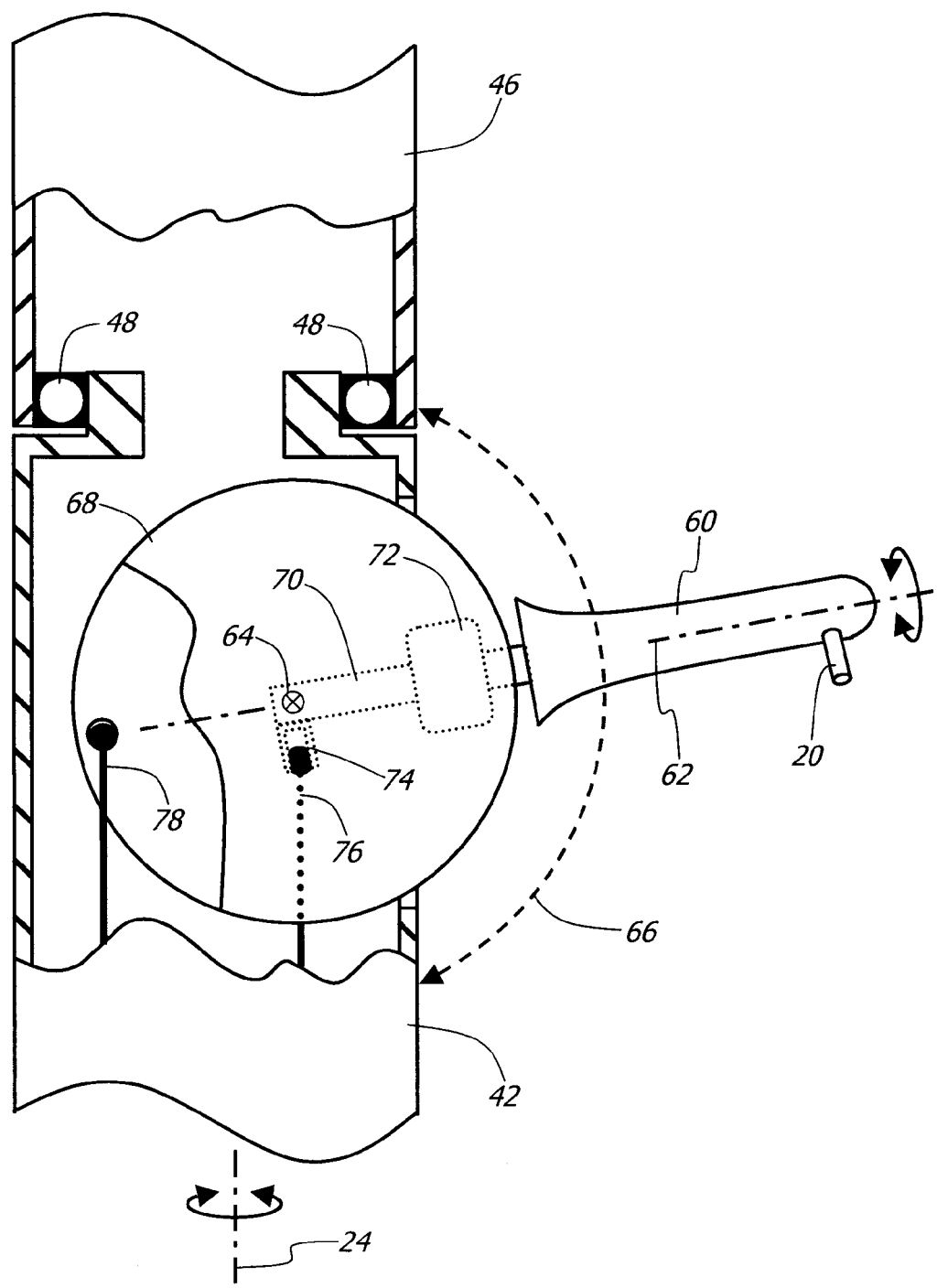
FIG. 3 is a cutaway view of an integrated mechanical three degree of freedom direction and rotation handle and coinciding pointer assembly implemented with push-pull rods according to an embodiment of the present invention.

FIG. 3 illustrates another embodiment of an integrated mechanical three degree of freedom handle and coinciding pointer assembly. A lever 60 with an orientation indicator 20 can rotate about a first axis 62 and swivel backwards and forwards about a second axis 64 over a limited range 66. The lever 60 is attached to a disk 68 through a shaft 70 and a bearing 72. The disk 68 rotates about the second axis 64. Rotation of the lever 60 about the first axis 62 causes rotation about the shaft 70 which through a coupling 74 transmits generally linear motion to a first push-pull rod 76 which controls instrument orientation. Swiveling the lever 60 about the second axis 64 causes rotation of the disk 68 which transmits generally linear motion to a second push-pull rod 78 which controls instrument working direction. The entire handle-pointer assembly can be used to rotate the forward portion of the instrument frame 42 relative to the backward portion 46 about a third axis 24, allowing the user to select working direction and orientation by pointing the lever 60 and spinning it about the first axis 62.

Figure 4:
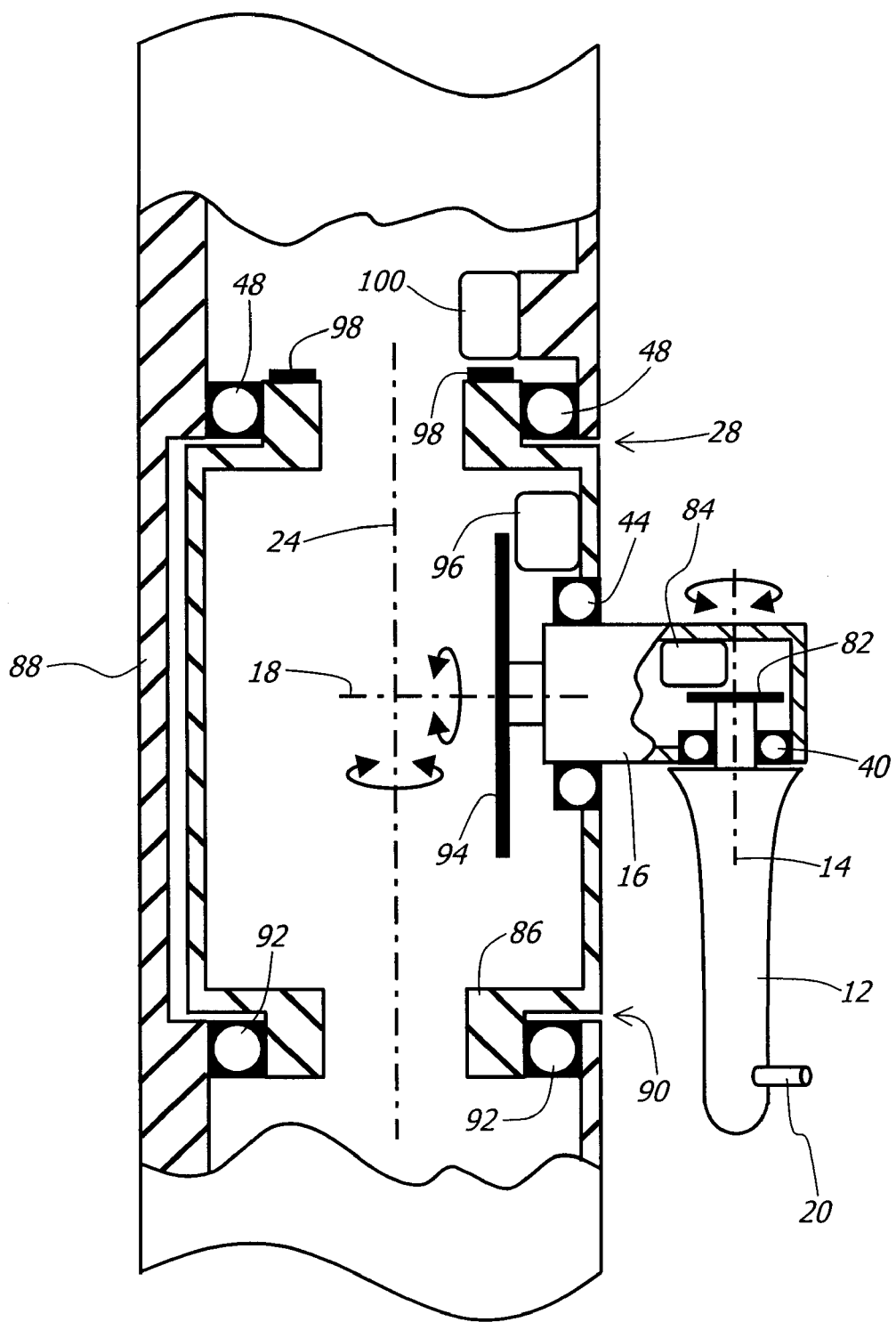
FIG. 4 is a cutaway view of an integrated electromechanical three degree of freedom direction and rotation handle and coinciding pointer assembly implemented with encoders and sensors according to an embodiment of the present invention.

FIG. 4 shows an embodiment of an integrated electromechanical three degree of freedom handle and coinciding pointer assembly. In this embodiment, the handle-pointer assembly controls the instrument mechanics through sensors that send signals to actuators in the endoscopic instrument. In this case, the handle-pointer assembly is not necessarily attached directly to the instrument endoscopic. A handle 12, which has a rotational indicator 20, is outfitted with a first disk encoder 82. Rotation of the handle 12 about a first axis 14 causes a corresponding rotation of the disk encoder 82, and this rotation is sensed by a first sensor 84 attached to a base 16. The base 16 is connected to a carriage 86 which is anchored to a frame 88 by an upper rotary joint 28 with a bearing 48, and a lower rotary joint 90 with a bearing 92. A second encoder disk 94 allows a second sensor 96 to sense rotation of the base 16 about a second axis 18. The carriage 86 can be rotated relative to the instrument frame 88 about a third axis 24, and such rotation can be monitored by a third sensor 98 which reads a ring encoder 100. The sensors 84, 96, 98 send information through a control system to actuators in the endoscopic instrument to mechanically control the working vector. In a similar alternative embodiment actuators might not be involved if the endoscopic instrument utilizes purely electronic operation.

Figure 5:
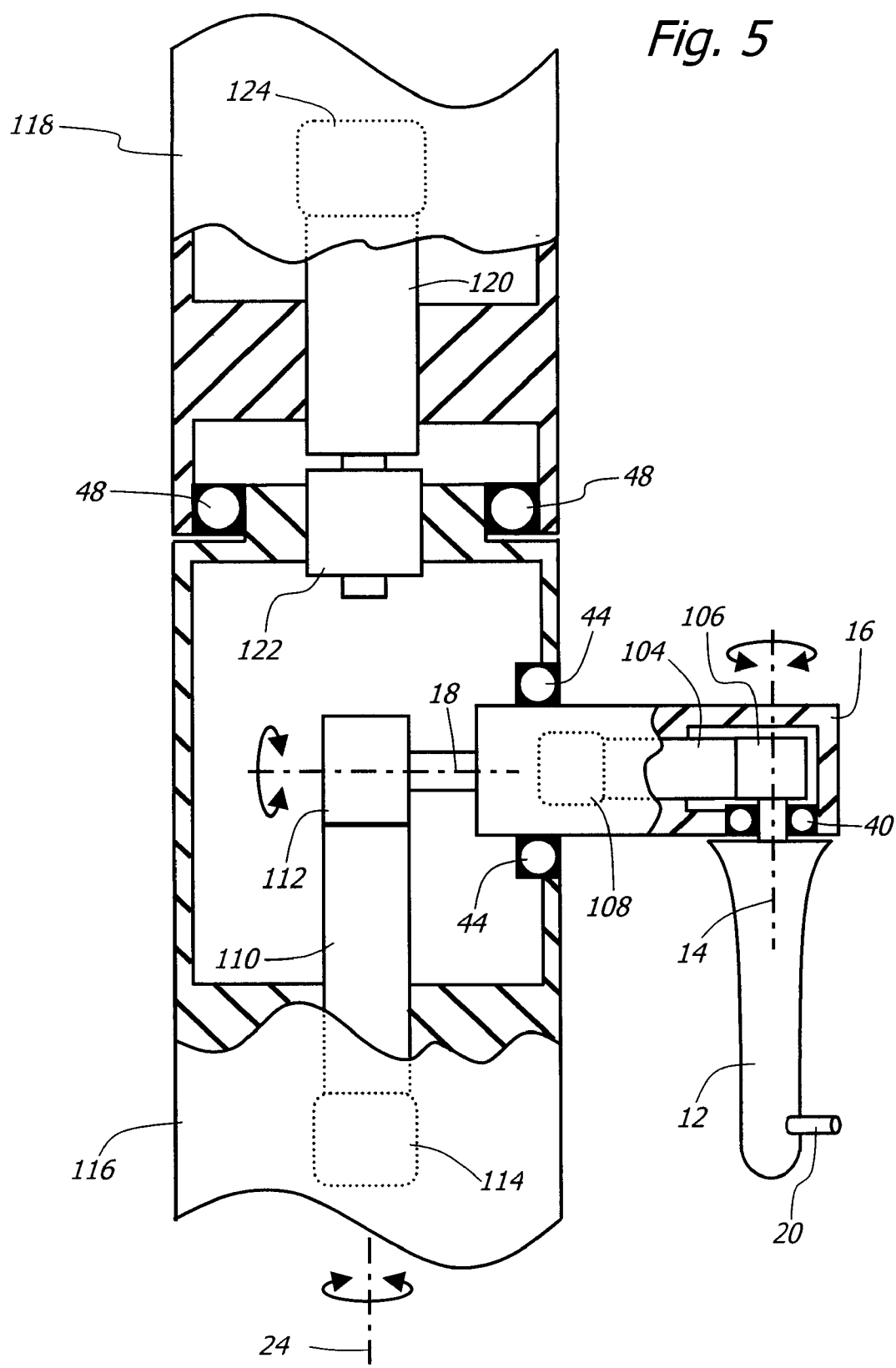
FIG. 5 is a cutaway view of an electromechanical three degree of freedom direction and rotation pointer assembly implemented with motors and encoders according to an embodiment of the present invention.

FIG. 5 illustrates embodiment of an integrated electromechanical three degree of freedom pointer assembly. In this embodiment the pointer assembly functions mainly as a passive pointer which automatically tracks the working vector (not shown) of an endoscopic instrument based on user input from an external device such as a keyboard or a joystick, although it could be used as a control handle as well. A handle 12 with an orientation indicator 20 is actuated by a first motor 104 through a first 90-degree gear box 106. The first motor 104 is outfitted with a first encoder 108, which keeps track of the rotational position of the pointer handle 12 about a first axis 14. The pointer handle 12 is attached to a base 16 which is actuated by a second motor 110 through a second 90-degree gear box 112. A second encoder 114 senses the rotational position of the base 16 about a second axis 18. The entire pointer assembly is attached to a movable frame 116 which can be rotated relative to a fixed frame 118 about a third axis 24 by a third motor 120. The third motor 120 is connected to the movable frame 116 by a coupling 122. A third encoder 124 senses the rotational position of the movable frame 116 about the third axis 24. A computerized control system (not shown) operates the motors 104, 110, 120 to keep the direction of the handle and the orientation of the orientation indicator aligned with the working vector (not shown).

Figure 6:
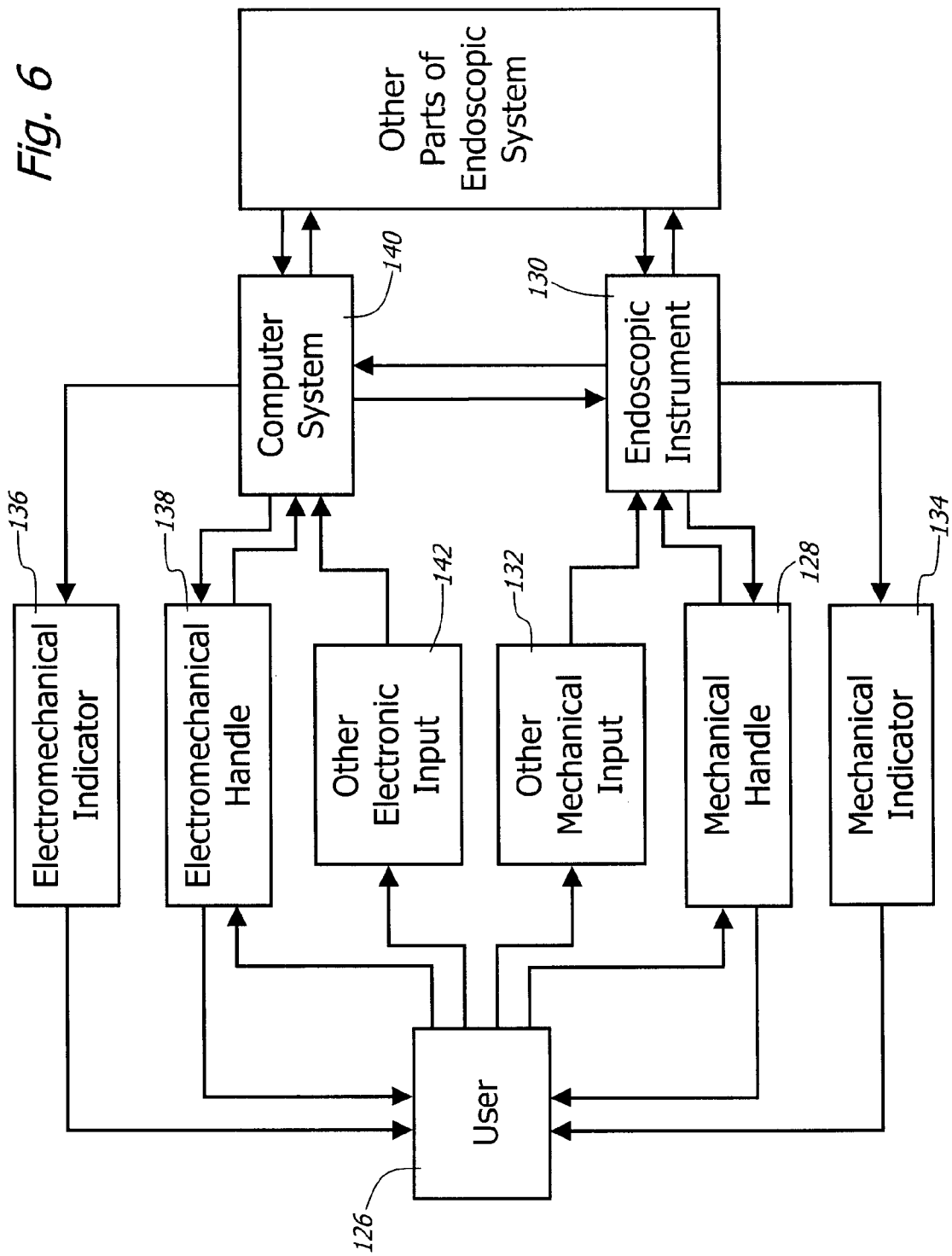
FIG. 6 is a schematic overview of how a user interacts with an endoscopic system through the handle and pointer assemblies of the present embodiment.

FIG. 6 shows how a user 126 interacts with a basic endoscopic instrument system by using the control handle and pointer assemblies described herein, with reference to either mechanical or electromechanical interactions. In a system driven by a mechanical handle 128, as represented in FIGS. 2 and 3, a movement of the handle 128 by the user 126 is directly transmitted to an endoscopic instrument 130. The new configuration of the instrument 130 is relayed back to the user 126 by the corresponding new handle configuration. There are also embodiments which use other mechanical input devices 132 such as knobs or triggers that do not inherently show the user 126 the instrument configuration, which is instead relayed back to the user with a mechanical or an electromechanical indicator 134, 136. In a system controlled with an electromechanical handle 138, as shown in FIGS. 4 and 5, movement of the handle is registered by sensors connected to a computer system 140, which adjusts the endoscopic instrument 130 correspondingly. As in the mechanical case, the adjusted configuration of the endoscopic instrument 130 is relayed back to the user 126 by the physical position of the handle 138. Other electronic input devices 142 such as a keyboard or a joystick could be used as well. In such cases information is conveyed back to the user 126 through the computer system 140 and an electromechanical indicator 136 or a mechanical indicator 134.

The systems linking such handle and pointer assemblies to the rest of the instrument may operate through any mechanical, electromechanical, or electronic means that satisfy the operating conditions listed without departing from the scope of the invention. Purely mechanical systems rely on components such as gears, shafts, cables, levers, etc. to convey motion and forces within the instrument. Electromechanical systems use electronic components such as motors, sensors, and encoders in addition to mechanical components.

The present invention is intended for use either as an attached device, located on the body of the instrument, or as a separate control device, located off the body of the endoscopic instrument. A separate control handle or pointer could be connected to the endoscopic system using either mechanical or electronic means. Wireless communications such as radio or infrared signals could be used without departing from the scope of the invention.

Accordingly, the present invention provides the user with integrated intuitive control of multiple degrees of freedom of an endoscopic instrument, an effective and intuitive representation of the direction and orientation of the working vector of an endoscopic instrument, and a better understanding of the overall spatial configuration of the instrument. The present invention also provides other advantages, such as a clear relationship between two or more distinct working configurations. The present invention could also be used to provide a more comfortable user interface, which does not necessarily have to coincide with the actual mechanics of the endoscopic instrument, and to provide a consistent control scheme for multiple instruments.

The present invention has been described above in terms of presently preferred embodiments so that an understanding of the present invention can be conveyed. However, there exist many possible configurations for an integrated multi-degree-of-freedom handle or pointer. Many structural and material variations are possible, as are variations in application. For example, in the case of a multi-jointed endoscopic instrument, the handle-pointer assembly may consist of several segments with multiple degrees of freedom to accurately depict the changes at the tip of the instrument. Further, while the examples were given with respect to instruments for use in surgical procedures, the present invention would be equally applicable to borescopes or borescopic tools for use within various mechanical structures. The scope of the present invention should therefore not be limited by the embodiments illustrated, but rather it should be understood that the present invention has wide applicability to endoscopic procedures in general. All modifications, variations, or equivalent elements and implementations that are within the scope of the appended claims should therefore be considered within the scope of the invention.

We claim:

1. An apparatus for aiding in the interpretation and control of a variable direction-of-view endoscopic visualization instrument comprising at least two degrees of freedom, wherein said endosoopic visualization instrument has a distal working vector and a working orientation about said working vector, said apparatus comprising:

a handle for controlling the direction of said working vector of said endoscopic visualization instrument;

a pointer that indicates a direction, wherein said pointer coincides with said handle;

a feature on said handle that indicates a rotational orientation about said direction of said pointer;

a first linking system connecting said pointer to said endoscopic visualization instrument, wherein said direction of said pointer corresponds to said direction of said working vector, and wherein changes to said direction of said pointer are equivalent to changes to said direction of said working vector; and a second linking system connecting said handle to said endoscopic instrument, wherein said rotational orientation of said feature corresponds to said working orientation, and wherein changes to said rotational orientation of said feature are equivalent to changes to said working orientation.

2. The apparatus of claim 1 wherein said first linking system is mechanical.

3. The apparatus of claim 1 wherein said first linking system is electro-mechanical.

4. The apparatus of claim 1 wherein said second linking system is mechanical.

5. The apparatus of claim 1 wherein said second linking system is electro-mechanical.

6. The apparatus of claim 1 wherein said working orientation of said endoscopic visualization instrument can be adjusted using said handle.

7. An apparatus for aiding in the interpretation of a variable direction-of-view endoscopic visualization instrument comprising at least two degrees of freedom, wherein said endoscopic visualization instrument has a distal working vector and a working orientation about said working vector, said apparatus comprising:

a pointer that indicates a direction;

a feature on said pointer that indicates a rotational orientation about said direction of said pointer;

a first linking system connecting said pointer to said endoscopic visualization instrument, wherein said direction of said pointer corresponds to said direction of said working vector, and wherein changes to said direction of said pointer are equivalent to changes to said direction of said working vector; and a second linking system connecting said feature to said endoscopic instrument, wherein said rotational orientation of said feature corresponds to said working orientation, and wherein changes to said rotational orientation of said feature are equivalent to changes to said working orientation.

8. The apparatus of claim 7 wherein said first linking system is mechanical.

9. The apparatus of claim 7 wherein said first linking system is electro-mechanical.

10. The apparatus of claim 7, wherein said second linking system is mechanical.

11. The apparatus of claim 7, wherein said second linking system is electro mechanical.

12. An apparatus for aiding in the interpretation and control of a variable direction-of-view endoscopic visualization instrument comprising at least two degrees of freedom, wherein said endoscopic visualization instrument has a distal working vector and a working orientation about said working vector, said apparatus comprising:

an input means for controlling the direction of said working vector of said endoscopic visualization instrument;

a first indicating means for indicating a direction, wherein first indicating means coincides with said input means;

a second indicating means on said input means for indicating a rotational orientation about said direction of said first indicating means;

a first linking means for connecting said first indicating means to said endoscopic visualization instrument, wherein said direction of said first indicating means corresponds to said direction of said working vector, and wherein changes to said direction of said first indicating means are equivalent to changes to said direction of said working vector, and a second linking means for connecting said second indicating means to said endoscopic instrument, wherein said rotational orientation of said second indicating means corresponds to said working orientation, and wherein changes to said rotational orientation of said second indicating means are equivalent to changes to said working orientation.

13. An apparatus for aiding in the interpretation of a variable direction-of-view endoscopic visualization instrument comprising at least two degrees of freedom, wherein said endoscopic visualization instrument has a distal working vector and a working orientation about said working vector, said apparatus comprising:

a first indicating means for indicating a direction;

a second indicating means on said first indicating means for indicating a rotational orientation about said direction of said first indicating means;

a first linking means for connecting said first indicating means to said endoscopic visualization instrument, wherein said direction of said first indicating means corresponds to said direction of said working vector, and wherein changes to said direction of said first indicating means are equivalent to changes to said direction of said working vector; and a second linking means for connecting said second indicating means to said endoscopic instrument, wherein said rotational orientation of said second indicating means corresponds to said working orientation, and wherein changes to said rotational orientation of said second indicating means are equivalent to changes to said working orientation.

* * * * *